US012582834B2

(12) United States Patent
Kim et al.

(10) Patent No.: US 12,582,834 B2
(45) Date of Patent: Mar. 24, 2026

(54) IN VIVO IMPLANTABLE NERVE STIMULATION PLATFORM AND NERVE STIMULATION METHOD USING THE SAME

(71) Applicant: RESEARCH & BUSINESS FOUNDATION SUNGKYUNKWAN UNIVERSITY, Suwon-si (KR)

(72) Inventors: Tae-Il Kim, Suwon-si (KR); Seunghwan Choy, Suwon-si (KR); Yei Hwan Jung, Suwon-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 990 days.

(21) Appl. No.: 17/739,854

(22) Filed: May 9, 2022

(65) Prior Publication Data

US 2022/0370825 A1     Nov. 24, 2022

(30) Foreign Application Priority Data

May 18, 2021     (KR) ........................ 10-2021-0063801

(51) Int. Cl.
*A61N 5/06*          (2006.01)
*A61N 5/00*          (2006.01)

(52) U.S. Cl.
CPC ......... *A61N 5/0622* (2013.01); *A61N 5/0601* (2013.01); *A61N 2005/005* (2013.01); *A61N 2005/0627* (2013.01); *A61N 2005/0651* (2013.01); *A61N 2005/0662* (2013.01)

(58) Field of Classification Search
CPC ................ A61N 5/0601; A61N 5/0622; A61N 2005/005; A61N 2005/0627; A61N 2005/0651; A61N 2005/0662

USPC ............................................................ 607/3
See application file for complete search history.

(56) References Cited

U.S. PATENT DOCUMENTS

| | | | |
|---|---|---|---|
| 7,288,108 B2 | 10/2007 | DiMauro et al. | |
| 9,401,625 B2* | 7/2016 | Zottola ................... | H02J 50/12 |
| 2007/0043404 A1* | 2/2007 | Deimling ............. | A61N 1/0534 |
| | | | 607/61 |
| 2015/0119794 A1* | 4/2015 | Peyman ............... | A61N 5/0622 |
| | | | 604/20 |
| 2017/0326381 A1* | 11/2017 | Kozai ................... | A61N 1/0551 |
| 2019/0030190 A1* | 1/2019 | Peyman ................... | A61K 9/51 |
| 2022/0146076 A1* | 5/2022 | Bourke, Jr. ........ | C09K 11/7701 |

FOREIGN PATENT DOCUMENTS

JP          2007-50258 A          3/2007

OTHER PUBLICATIONS

Kim, Tae-il, et al. "Injectable, Cellular-Scale Optoelectronics with Applications for Wireless Optogenetics." Science 340.6129 (2013): (48 pages in English).
Kim, Tae Soo, et al. "Ultra-Lightweight, Flexible InGaP/GaAs Tandem Solar Cells with a Dual-Function Encapsulation Layer." ACS Applied Materials & Interfaces 13.11 (2021): 13248-13253.

* cited by examiner

*Primary Examiner* — Ahmed M Farah
(74) *Attorney, Agent, or Firm* — LEX IP MEISTER, PLLC

(57)          ABSTRACT

Provided is an in vivo implantable nerve stimulation platform which includes: a light source emitting light having a plurality of wavelength bands; and a photoelectric generator generating electricity for stimulating a nerve or a tissue by the light emitted from the light source, in which the light source and the photoelectric generator are implanted in vivo.

10 Claims, 8 Drawing Sheets

3 mm (Positive pole)

360 um (Negative pole)

| $V_{OC}$ (V) | 2.301 |
|---|---|
| $J_{SC}$ (mA/cm$^2$) | 12.703 |
| Fill Factor (%) | 85.844 |
| Efficiency (%) | 25.087 |

464nm LED

530nm LED

630nm LED

IN VIVO IMPLANTABLE NERVE STIMULATION PLATFORM AND NERVE STIMULATION METHOD USING THE SAME

FIELD

The present disclosure relates to an in vivo implantable nerve stimulation platform and a server stimulation method using the same.

DESCRIPTION OF THE RELATED ART

Electric nerve stimulation treatment is known as an effective nerve stimulation method that can be used in clinical trials. However, in order to stimulate a plurality of nerves at the same time, it is necessary to integrate a plurality of electrodes, and since there is a plurality of wires to electrically connect the plurality of electrodes, when an element that can simultaneously stimulate the plurality of nerves is inserted into the tissue, there is a disadvantage in that the volume increases, and there may be problems such as inflection, etc., at an insertion portion.

In order to solve such a problem, new biological technologies using light or heat, such as optogenetics or thermogenetics, which perform gene manipulation for a brain cell to be sensitive to action of the light or heat, and then stimulate the nerve by applying the light or heat are being developed. However, when a foreign protein introduced in vivo is in contact with an immune substance in vivo for the gene manipulation, a foreign substance immune response is caused and a metabolic process is performed, and as result, there is a disadvantage in that a chronic impact can be exerted on the body even with gene modification.

Further, an electric stimulation method, the optogenetics and the thermogenetics which are the above-described nerve stimulation methods have a disadvantage in that all targeted cells are not expressed at the same level, but an excitement degree of the brain cell deviates form a normal numerical value or it is difficult to control the excitement degree of the brain cell.

U.S. Pat. No. 7,288,108 as a technology which becomes a background of the present disclosure relates to a red light implant for treating Parkinson's disease. The patent application inserts an LED emitting red light and stimulates a nerve for treating the Parkinson's disease by using the red light.

SUMMARY

An object to be solved by the present disclosure is to provide an in vivo implantable nerve stimulation platform capable of selectively stimulating nerves and tissues of multiple points by using a photoelectric effect.

Further, an object to be solved by the present disclosure is to provide a nerve stimulation method using the in vivo implantable nerve stimulation platform.

However, a technical object to be achieved by an exemplary embodiment of the present disclosure is not limited to the technical objects and there may be other technical objects.

As a technical means for solving the technical problem, according to a first aspect of the present disclosure, provided is an in vivo implantable nerve stimulation platform which includes: a light source emitting light having a plurality of wavelength bands; and a photoelectric generator generating electricity for stimulating a nerve or a tissue by the light emitted from the light source, in which the light source and the photoelectric generator are implanted in vivo.

According to an implementation example of the present disclosure, the photoelectric generator may generate electricity according to a wavelength or an intensity of the light emitted from the light source, but is not limited thereto.

According to an implementation example of the present disclosure, the photoelectric generator may generate the electricity according to a distance between the photoelectric generator and the light source, but is not limited thereto.

According to an implementation example of the present disclosure, there may be a plurality of photoelectric generators and the plurality of photoelectric generators may be disposed spaced apart from each other, but is not limited thereto.

According to an implementation example of the present disclosure, the first photoelectric generator may generate the electricity according to light having a first wavelength band or light having a first intensity, but is not limited thereto.

According to an implementation example of the present disclosure, the second photoelectric generator may generate the electricity according to light having a second wavelength band or light having a second intensity, but is not limited thereto.

According to an implementation example of the present disclosure, a size of the first wavelength band may be larger than that of the second wavelength band, but is not limited thereto.

According to an implementation example of the present disclosure, the first intensity may be smaller than the second intensity, but is not limited thereto.

According to an implementation example of the present disclosure, the first photoelectric generator may be spaced apart from the light source by a first distance, but is not limited thereto.

According to an implementation example of the present disclosure, the second photoelectric generator may be spaced apart from the light source by a second distance, but is not limited thereto.

According to an implementation example of the present disclosure, a current density of the electricity generated by the photoelectric generator may be 10 $\mu$A/cm$^2$ to 1,000 $\mu$A/cm$^2$, but is not limited thereto.

According to an implementation example of the present disclosure, the photoelectric generator may include InGaP and GaAs, but are not limited thereto.

According to an implementation example of the present disclosure, the light source may include an LED, a circuit unit driving the LED, an antenna supplying an operation signal to the circuit unit, a heat dissipation layer dissipating heat generated from the LED, and a protection layer protecting the LED, but is not limited thereto.

According to an implementation example of the present disclosure, the wavelength of the light emitted from the light source may be 400 nm to 700 nm, but is not limited thereto.

According to an implementation example of the present disclosure, the in vivo implantable nerve stimulation platform may further include a control unit controlling the operation of the implantable light source from the outside of the in vivo, but is not limited thereto.

Further, according to a second aspect of the present disclosure, provided is a nerve stimulation method using the in vivo implantable nerve stimulation platform according to the first aspect, which includes: generating, by a control unit, a control signal for driving a light source and transmitting the generated control signal to the light source; generating, by the light source, light having a predetermined wavelength or intensity based on the control signal; and generating, by a photoelectric generator, electricity according to a wavelength or an intensity of the generated light.

According to an implementation example of the present disclosure, there may be a plurality of photoelectric generators and the plurality of photoelectric generators may be disposed spaced apart from each other, but is not limited thereto.

According to an implementation example of the present disclosure, the step of transmitting, by the control unit, the control signal to the light source may be performed by the wireless communication, but the present disclosure is not limited thereto.

The problem solving means is just exemplary, and should not be interpreted as an intention of limiting the present disclosure. In addition to the exemplary example, an additional example may exist in drawings and a detailed description of the present disclosure.

The conventional nerve stimulation platform is performed by a method such as electric stimulation, optogenetics, and thermogenetics. However, the electric stimulation method requires integration of multiple electrodes and multiple electric wires therefor, so in the nerve stimulation platform for electric stimulation, a volume is large and infection, etc., may occur when implanting the nerve stimulation platform in vivo. Further, the optogenetics and the thermogenetics require the gene manipulation of the cell to be sensitive to the action of the light or heat, and as a result, a chronic problem may occur due to an ethical problem and genetic modification. Moreover, the conventional method has a disadvantage in that all cells to be stimulated are not stimulated at the same level, and it is difficult to control the excitement degree of the cell.

According to the solving means of the present disclosure, the in vivo implantable nerve stimulation platform according to the present disclosure includes a light source such as an in vivo implantable light emitting micro integration type diode, and a photoelectric generator converting light generated from the light source into electric energy. As a result, the in vivo implantable nerve stimulation platform according to the present disclosure can be on/off-controlled externally to overcome a disadvantage of the conventional nerve stimulation platform without a need of multiple electric wires for controlling the light source or the electrode and without performing the gene manipulation, etc.

Further, the in vivo implantable nerve stimulation platform may selectively stimulate nerves in multiple portions from micro LED array light sources having a plurality of wavelengths at the same time or at a time difference.

Further, as the in vivo implantable nerve stimulation platform according to the present disclosure can be implanted to all portions in vivo, the in vivo implantable nerve stimulation platform can stimulate nerves other than the brain, and as a result, an exercise function can be restored.

Further, since the light source of the in vivo implantable nerve stimulation platform according to the present disclosure can be implanted between hemispheres of two cerebrums, and the photoelectric generator can be implanted by using a needle of a syringe, an infection risk can be reduced by minimizing an invasion.

However, an effect which can be obtained in the present disclosure is not limited to the effects, and there may be other effects.

BRIEF DESCRIPTION OF THE DRAWINGS

The above and other aspects, features and other advantages of the present disclosure will be more clearly understood from the following detailed description taken in conjunction with the accompanying drawings, in which:

FIG. 3 is a schematic view of a light source according to an implementation example of the present disclosure.

FIG. 4 is a schematic view of a photoelectric generator according to an implementation example of the present disclosure;

FIG. 10A to FIG. 100 are light-current-voltage (L-I-V) graphs of the light source according to an example of the present disclosure.

DETAILED DESCRIPTION OF THE EMBODIMENT

Figures 1, 2:
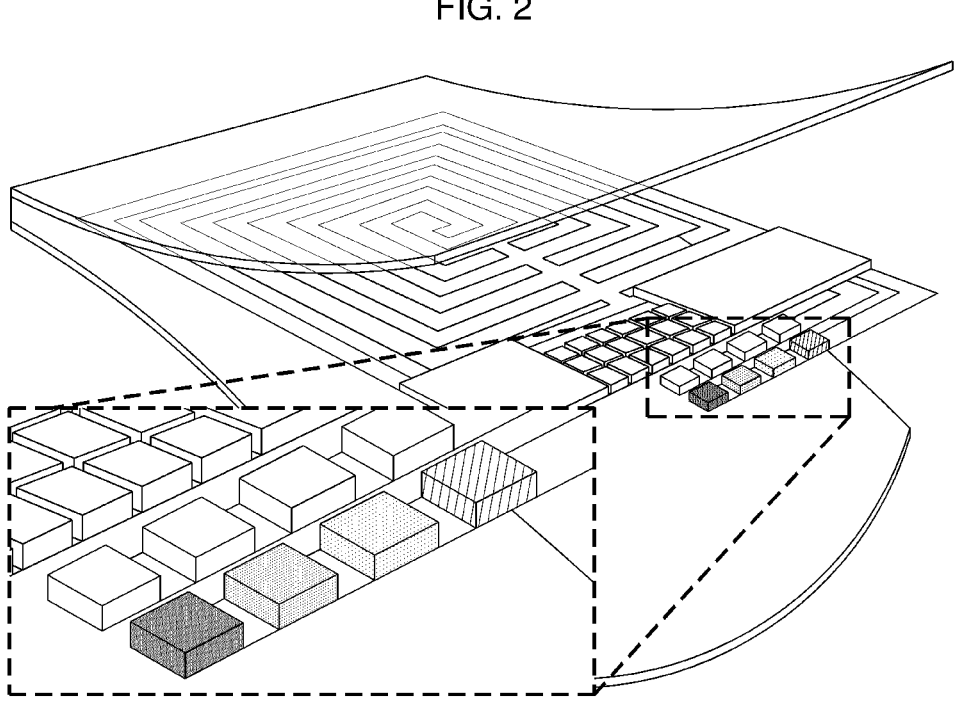
FIG. 1 is a schematic view of an in vivo implantable nerve stimulation platform according to an implementation example of the present disclosure.
FIG. 2 is a schematic view of a light source according to an implementation example of the present disclosure.

Hereinafter, examples of the present disclosure will be described in detail so as to be easily implemented by those skilled in the art, with reference to the accompanying drawings.

However, the present disclosure may be implemented in various different forms and is not limited to examples described herein. In addition, in the drawings, in order to clearly describe the present disclosure, a part not related to the description is not omitted and like reference numerals designate like elements throughout the specification.

Throughout the present disclosure, when it is described that a part is "connected" with another part, it means that the part may be "directly connected" with the another part and the parts may be "electrically or mechanically connected" to each other with still another element interposed therebetween.

Throughout the present disclosure, it will be understood that when a member is referred to as being "on", "in upper portion", "in upper end", "below", "in lower portion", and "in lower end" another member, it may be directly on the other member or intervening members may also be present.

Throughout the present disclosure, unless explicitly described to the contrary, a case where any part "includes" any component will be understood to imply the inclusion of stated components but not the exclusion of any other component.

"Approximately" "substantially", etc., which are terms of degrees used in the present disclosure is used as a numerical value or a meaning close to the numerical value when unique manufacturing and material allowable errors are presented in the mentioned meaning, and used for preventing unscrupulous infringer from using the disclosed contents in which an accurate or absolute numerical value is mentioned in order to assist understanding of the present disclosure. Further, throughout the present disclosure, "step (of~)" or "step of~" does not mean "step for".

Throughout the present disclosure, a term "combination thereof" included in an expression of the Makushi form which means one or more mixtures or combinations selected form the group consisting of components disclosed in the expression of the Makushi form means including at least one selected from the group consisting of the components.

Through the present disclosure, a disclosure of "A and/or B" means "A or B, or, A and B".

Hereinafter, an in vivo implantable nerve stimulation platform and a nerve stimulation method using the same according to the present disclosure will be described in detail with reference to implementation examples and examples, and drawings. However, the present disclosure is not limited to the implementation examples and examples, and drawings.

As a technical means for achieving the technical object, a first aspect of the present disclosure relates to an in vivo implantable nerve stimulation platform which includes a light source 100 emitting light having a plurality of wavelength bands, and a photoelectric generator 200 generating electricity stimulating a nerve or a tissue by light 300 emitted from the light source 100, in which the light source 100 and the photoelectric generator 200 are implanted in vivo. Although described below, the in vivo implantable nerve stimulation platform means a system for neurostimulation treatment.

The conventional nerve stimulation treatment as a medical technique for treating a specific disease by stimulating the cell such as the nerve or tissue may be subdivided into vagus neuroma stimulation, brain stimulation, etc. The nerve stimulation treatment may be performed by a method such as electric stimulation, optogenetics, and thermogenetics. Among them, the electric stimulation is known as an effective nerve stimulation treatment method to be used even in clinical trials, but, in order to stimulate multiple nerves at the same time, since integration of a plurality of electrodes and a plurality of electric wires therefor are required, a volume of an element for nerve stimulation treatment increases, and when the element is inserted into an affected tissue, an infection problem by the size of the element may occur. Further, in the case of nerve stimulation treatment using new biological technologies using light or heat, such as optogenetics, and thermogenetics, a gene manipulation which makes a nerve cell such as a brain cell, be sensitive by an action of the light or heat is required, but a foreign protein introduced in vivo for the gene manipulation causes a foreign substance immune response, and passes through a metabolic process, so only gene modification may exert a chronic impact on a patient, and there is a disadvantage in that all cells of the affected tissue are not stimulated at the same level and it is difficult to control an excitement degree of the cell to maintain a normal numerical value.

However, the in vivo implantable nerve stimulation platform according to the present disclosure uses light similarly to the optogenetics, but stimulates the nerve through the electricity generated by using a photoelectric effect. By using the photoelectric effect, the plurality of electric wire are not required, and the nerve may be stimulated with the light without the gene manipulation.

FIG. 1 is a schematic view of an in vivo implantable nerve stimulation platform according to an implementation example of the present disclosure. Specifically, FIG. 1 means an in vivo implantable nerve stimulation platform when the light source 100 of the nerve stimulation platform is implanted between hemispheres of cerebrums in vivo, and two photoelectric generators 200 are disposed at predetermined locations in a cerebral cortex.

Although described below, the photoelectric generator 200 may selectively react only to light of a specific wavelength band. Accordingly, the light source 100 simultaneously or selectively emits first light 310 for stimulating a first photoelectric generator 210 and second light 320 for stimulating a second photoelectric generator 220 to selectively stimulate the first photoelectric generator 210 and the second photoelectric generator 220.

According to an implementation example of the present disclosure, the photoelectric generator 200 may generate electricity according to a wavelength or an intensity of the light 300 emitted from the light source 100, but is not limited thereto.

According to an implementation example of the present disclosure, the photoelectric generator 200 may generate the electricity according to a distance between the photoelectric generator 200 and the light source 100, but is not limited thereto.

The wavelength or intensity of light which reaches the photoelectric generator 200 may be determined according to the wavelength or the intensity of the light emitted from the light source 100 or the distance between the light source 100 and the photoelectric generator 200. In this case, the photoelectric generator 200 may generate the electricity by reacting with light having a specific wavelength, and control the intensity of the light and the intensity of the electricity generated from the photoelectric generator 200 through the distance the light source 100 and the photoelectric generator 200.

Although described below, since the photoelectric generator 200 may have a photoelectric effect like a solar cell, when the light 300 emitted from the light source 100 is irradiated to the photoelectric generator 200, the photoelectric generator 200 may generate the electricity and the nerve or the tissue may be stimulated through the electricity.

According to an implementation example of the present disclosure, there may be a plurality of photoelectric generators 200 and the plurality of photoelectric generators 200 may be disposed spaced apart from each other, but is not limited thereto.

As described above, when the neurostimulation treatment is performed using the in vivo implantable nerve stimulation platform, it is necessary to stimulate cells at two portions or more. To this end, the plurality of photoelectric generators 200 may be installed in the nerve or the tissue. In this case, the plurality of photoelectric generators 200 may be classified into the first photoelectric generator 210 and the second photoelectric generator 220, and the first photoelectric generator 210 and the second photoelectric generator 220 may electrically stimulate nerves performing the same role or nerves performing different roles.

According to an implementation example of the present disclosure, the first photoelectric generator 210 may generate the electricity according to light having a first wavelength band or light having a first intensity, but is not limited thereto.

According to an implementation example of the present disclosure, the second photoelectric generator 220 may generate the electricity according to light having a second wavelength band or light having a second intensity, but is not limited thereto.

In this regard, the light having the first wavelength band or the light having the first intensity means the first light 310 of FIG. 1 and the light having the second wavelength band or the light having the second intensity means the second light 320 of FIG. 1.

According to an implementation example of the present disclosure, a size of the first wavelength band may be larger than that of the second wavelength band, but is not limited thereto.

According to an implementation example of the present disclosure, the first intensity may be smaller than the second intensity, but is not limited thereto.

Since the first photoelectric generator 210 may react only with the light having the first wavelength band and the second photoelectric generator 220 may react only with the light having the second wavelength band, operations of the first and second photoelectric generators 210 and 220 may be controlled by adjusting the wavelength or intensity of the light emitted from the light source 100. For example, when the light source 100 emits light of green light (530 nm), the first photoelectric generator 210 may generate the electricity, but the second photoelectric generator 220 may not generate the electricity. Further, as an example, when the light source 100 emits light of red light (630 nm), the second photoelectric generator 220 may generate the electricity.

Further, as an example, the first photoelectric generator 210 may generate the electricity by the light of the green light (530 nm) and the second photoelectric generator 220 may generate the electricity by the light of the red light (630 nm). In this regard, when the first and second photoelectric generators 210 and 220 are the same material, the second photoelectric generator 220 may generate the electricity even by the green light (530 nm) by the photoelectric effect. In this case, by adjusting the intensities of the first light 310 and the second light 320, the electricity may be adjusted not to be generated by an unnecessary photoelectric generator 200 by reducing the intensity of the light when stimulating a close distance.

Further, when the light source 100 emits both the light having the first wavelength band and the light having the second wavelength band, the electricity is simultaneously generated by the first photoelectric generator 210 and the second photoelectric generator 220 to electrically stimulate a plurality of nerves or tissues.

According to an implementation example of the present disclosure, the first photoelectric generator 210 may be spaced apart from the light source 100 by a first distance, but is not limited thereto.

According to an implementation example of the present disclosure, the second photoelectric generator 220 may be spaced apart from the light source 100 by a second distance, but is not limited thereto.

For example, when the first photoelectric generator 210 and the second photoelectric generator 220 are spaced from the light source 100 by the same interval, an angle between the first distance and the second distance may be more than 0° or equal to or less than 180°. In this case, the first photoelectric generator 210 and the second photoelectric generator 220 may selectively generate the electricity by the first light 310 and the second light 320, respectively, and the first light 310 and the second light 320 may have the same light intensity, but have the same wavelength band or different wavelength bands.

Further, as an example, when the size of the first distance is larger than that of the second distance, the angle between the first distance and the second distance may be equal to or more than 0°. When the angle between the first distance and the second distance is 0°, and the first photoelectric generator 210 and the second photoelectric generator 220 generate the electricity by the light having the same wavelength band, the first intensity which is the intensity of the light of the first light 310 may be larger than the second intensity which is the intensity of the light of the second light 320.

According to an implementation example of the present disclosure, the light source 100 and the photoelectric generator 200 may be positioned on a straight line, but are not limited thereto.

There may be cell tissues such as the brain, the nerve, the blood, and the muscle, between the light source 100 and the photoelectric generator 200, but the cell tissue scatters the light 300 emitted from the light source 100 to reduce the intensity of the light which reaches the photoelectric generator 200, thereby adjusting the intensity of the electricity.

When the number of types of a plurality of photoelectric generators 200 are three or more, respective photoelectric generators 200 may selectively generate the electricity by light of a specific wavelength band or light of the same wavelength band, but the present disclosure is not limited thereto.

According to an implementation example of the present disclosure, a current density of the electricity generated by the photoelectric generator 200 may be 10 $\mu A/cm^2$ to 1,000 $\mu A/cm^2$, but is not limited thereto. In this case, the current density of the electricity generated by the photoelectric generator 200 may be in proportion to the wavelength of the light irradiated by the photoelectric generator 200.

For example, when the red light having a wavelength of 630 nm is irradiated to the photoelectric generator 200, the current density of the generated electricity may be 500 $\mu A/cm^2$, when the green light having a wavelength of 530 nm is irradiated to the photoelectric generator 200, the current density of the generated electricity may be 116 $\mu A/cm^2$, and when the blue light having a wavelength of 464 nm is irradiated to the photoelectric generator 200, the current density of the generated electricity may be 30.8 $\mu A/cm^2$. When the current density of the electricity generated by the photoelectric generator 200 is less than 10 $\mu A/cm^2$, the nerve or tissue may not be stimulated and when the current density is more than 1,000 $\mu A/cm^2$, there is a problem in that an unnecessary nerve or tissue may be stimulated.

According to an implementation example of the present disclosure, voltage applied to the light source 100 may be 1 V to 4 V, but is not limited thereto. Preferably, the voltage applied to the light source 100 may be 1.5 V to 3.5 V, but is not limited thereto.

In order to increase the intensity of the light 300 emitted from the light source 100, high voltage may be applied to the light source. However, when the light source 100 is an LED, heat is generated from the LED by the voltage and when the voltage increases to a predetermined numerical value or more, there is a problem in that the intensity of the emitted light 300 may still decrease.

According to an implementation example of the present disclosure, an operation form of the photoelectric generator 200 may vary according to the wavelength of the light 300 emitted from the light source 100, the intensity of the emitted light 300, and the distance between the light source 100 and the photoelectric generator 200. In this regard, the intensity of the emitted light 300 may mean brightness and darkness degrees of the light, and may be a numerical value which is not related to energy according to the wavelength.

For example, since the photoelectric generator 200 may generate more electricity as the photoelectric generator 200 is closer to the light source 100, the intensity of the light 300 emitted from the light source 100 is adjusted to allow only the photoelectric generator 200 close to the light source 100 to generate meaningful electricity.

Figures 3, 4:
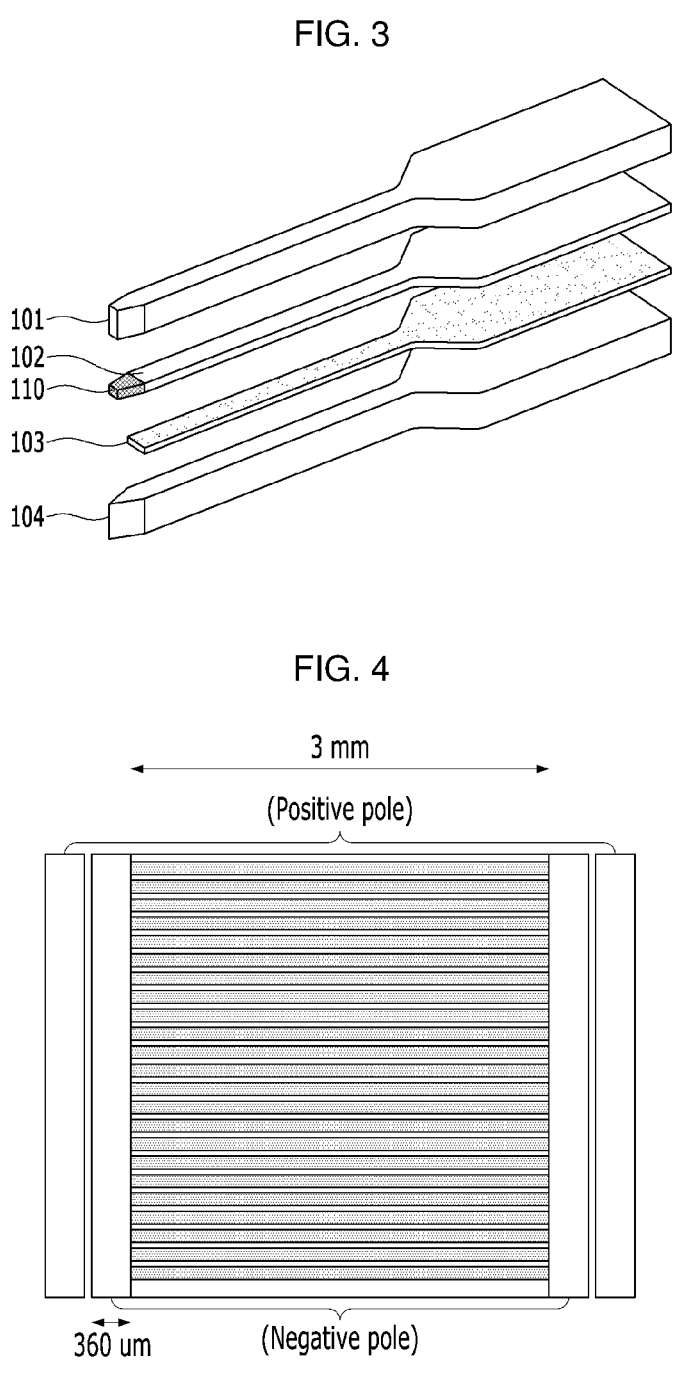

FIGS. 2 and 3 are schematic views of a light source 100 according to an implementation example of the present disclosure. Specifically, FIG. 3 is a diagram replicating a structure of the light source 100 in which the light source 100 is implanted in vivo.

According to an implementation example of the present disclosure, the light source 100 may include a circuit unit 102 in which the LED 110 is disposed at one terminal portion and an antenna (not illustrated) receiving a signal for controlling driving of the LED 110 is included in the other terminal portion, a heat dissipation layer 103 for dissipating heat generated from the circuit unit 102, and a protective layer 101 protecting the circuit unit 102, but the present disclosure is not limited thereto. In this regard, based on FIG. 3, one side of the circuit unit 102 may mean an 8-o'clock direction and the other side may mean a 2-o'clock direction, and the light source 100 may be inserted in one direction.

Referring to FIGS. 2 and 3, the LED 110 as a micro LED 110 may include red, green, and blue light emitting materials, and may be positioned at one terminal portion of the circuit unit 102, but is not limited thereto. In this case, the LED 110 may emit light selected from the group consisting of red light, green light, blue light, and a combination thereof, and having various wavelength bands.

Although described below, when a control unit 400 outside the in vivo transfers an operation signal to the circuit unit 102 through the antenna, the circuit unit 102 may determine driving of the LED 110 so as to emit light having a specific wavelength band. In this case, the heat generated from the circuit unit 102 may be dissipated to the outside by the heat dissipation layer 103, and as a result, damage to the nerve or tissue due to the heat generated from the light source 100 may be minimized.

According to an implementation example of the present disclosure, the heat dissipation layer 103 may be a BN, but is not limited thereto.

According to an implementation example of the present disclosure, the step of implanting the light source 100 in vivo may include a step of inserting an injection guide 104 in vivo, a step of forming the light source 100 including the heat dissipation layer 103, the circuit unit 102, and the protective layer 101 on the injection guide 104, and a step of implanting the light source 100 in vivo along the injection guide 104, but is not limited thereto.

The injection guide 104 according to the present disclosure is used for implanting the light source 100 in vivo, and the injection guide 104 guides the light source 100 to be implanted into an accurate location in vivo.

According to an implementation example of the present disclosure, the wavelength of the light emitted from the light source 100 may be 400 nm to 700 nm, but is not limited thereto.

Figure 5:
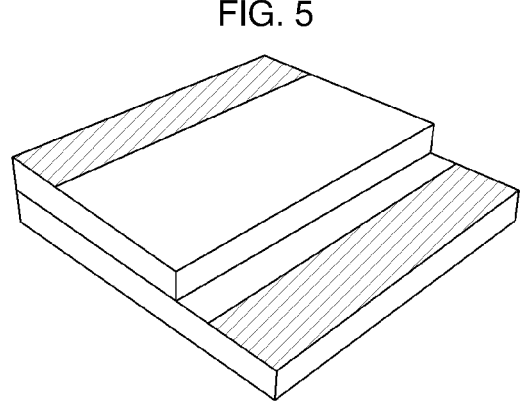
FIG. 5 is a schematic view of a photoelectric generator according to an implementation example of the present disclosure.

FIGS. 4 and 5 are schematic views of a photoelectric generator 200 according to an implementation example of the present disclosure.

The photoelectric generator 200 according to the present disclosure as an element converting the light into the electricity may have the same operation principle as the solar cell.

According to an implementation example of the present disclosure, the photoelectric generator 200 may have a tandem structure, but is not limited thereto.

The tandem structure according to the present disclosure may mean a structure in which two or more types of materials are dually bonded, and photoelectric conversion efficiency may increase as compared with a structure using one type of material.

According to an implementation example of the present disclosure, the photoelectric generator 200 may include InGaP and GaAs, but are not limited thereto. Preferably, the photoelectric generator 200 may have the tandem structure of GaAs/InGaP.

According to an implementation example of the present disclosure, the in vivo implantable nerve stimulation platform may further include a control unit 400 controlling the operation of the implantable light source 100 from the outside of the in vivo, but is not limited thereto.

The control unit 400 according to the present disclosure which is disposed outside in vivo unlike the light source 100 and the photoelectric generator 200 may wirelessly adjust on/off of the operation of the light source 100. An operation signal generated by the control unit 400 may be transferred to the circuit unit 102 through the antenna of the light source 100, and the LED 110 may emit light having a specific wavelength band according to the operation signal.

According to an implementation example of the present disclosure, the nerve or tissue may include a cell tissue of an in vivo portion selected from the group consisting of the cerebrum, the muscle, an endocrine system, a circulatory system, a urinary system, a reproductive system, a digestive system, a respiratory system, and combinations thereof, but is not limited thereto. For example, the nerve or tissue may mean the cerebral cortex.

Further, a second aspect of the present disclosure relates to a nerve stimulation method using the in vivo implantable nerve stimulation platform according to the first aspect, which includes generating a control signal for driving the light source 100 and transmitting the generated control signal to the light source 100 by the control unit 400, generating light having a predetermined wavelength or intensity based on the control signal by the light source 100, and generating electricity according to the wavelength or intensity of the generated light by the photoelectric generator 200.

A detailed description of redundant parts of the nerve stimulation method according to the second aspect of the present disclosure with the first aspect of the present disclosure is omitted, but even though the description is omitted, contents disclosed in the first aspect of the present disclosure may be equally applied to the second aspect of the present disclosure.

The in vivo implantable nerve stimulation platform may include the light source 100 and the photoelectric generator 200 disposed inside the living body, and the control unit 400 which is disposed outside the living body, and is capable of controlling the operation of the light source 100, and the control unit 400 may control the wavelength of the light emitted from the light source 100 through wireless communication.

Figure 6:
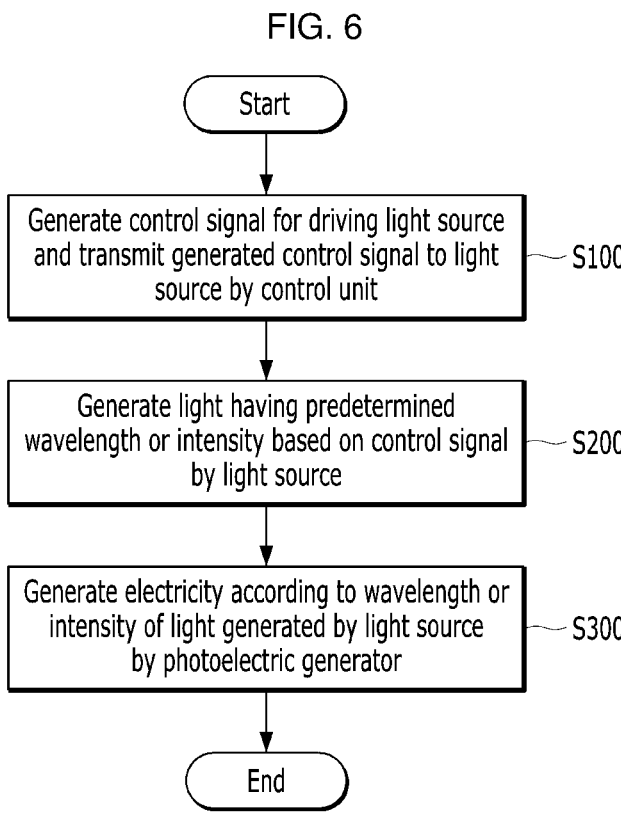
FIG. 6 is a flowchart of a nerve stimulation method according to an implementation example of the present disclosure.

FIG. 6 is a flowchart of a nerve stimulation method according to an implementation example of the present disclosure.

First, a control unit 400 generates a control signal for driving a light source 100, and transmits the control signal to the light source 100 (S100).

According to an implementation example of the present disclosure, the step of transmitting, by the control unit 400, the control signal to the light source 100 may be performed by the wireless communication, but the present disclosure is not limited thereto.

When the control unit 400 uses wired communication using the electric wire at the time of transmitting the signal to the light source 100, there may be a problem such as the volume of the electric wire, and an infection risk which may occur in the process of implanting the electric wire in vivo. Accordingly, the step of transmitting the control signal may be performed by the wireless communication.

According to an implementation example of the present disclosure, the wireless communication may include near-field communication (NFC) or far-field communication (FFC), but is not limited thereto. Preferably, the wireless communication may include the FFC.

The NFC according to the present disclosure may be used when the distance between the control unit 400 and the light source 100 is less than 10 cm, and has a disadvantage in that transmission efficiency of the signal is high, but the size of a receiving antenna should be large, and the locations of the control unit 400 and the antenna of the light source 100 should be present within a predetermined range. On the contrary, in the FFC according to the present disclosure, even though the distance between the control unit 400 and the light source 100 is more than 1 m and the control unit 400 and the antenna of the light source 100 are not present within the predetermined range, the operation signal of the control unit 400 may be transferred to the light source 100.

Subsequently, the light source 100 generates light having a predetermined wavelength or intensity based on the control signal (S200).

The light source 100 includes the LED 110 generating light, the antenna receiving the control signal, and the circuit unit 102 capable of controlling the driving of the LED 110 according to the control signal and having the LED 110 disposed at the end thereof. Accordingly, when the control signal is generated from the control unit 400, the antenna may transmit the control signal to the circuit unit 102, and the circuit unit 102 may control the driving of the LED 110 so as to emit light having a specific wavelength band or a specific intensity according to the control signal.

The LED 110 may emit light having a single wavelength band with a predetermined intensity, emit light having a plurality of wavelength bands with a predetermined intensity, emit the light having the single wavelength band with various intensities, or emit the light having the plurality of wavelength bands with various intensities, but is not limited thereto.

Subsequently, the photoelectric generator 200 generates the electricity according to the wavelength or intensity of the generated light (S300).

According to an implementation example of the present disclosure, there may be a plurality of photoelectric generators 200 and the plurality of photoelectric generators 200 may be disposed spaced apart from each other, but is not limited thereto.

The photoelectric generator 200 may transform the light 300 emitted from the light source 100 to the electricity, and the electricity may stimulate the nerve or tissue adjacent to the photoelectric generator 200. That is, the photoelectric generator 200 may stimulate the nerve or tissue by generating the electricity through the light irradiated from the light source 100.

According to an implementation example of the present disclosure, before performing the nerve stimulation method, a step of implanting the light source 100 in vivo and a step of implanting at least one photoelectric generator 200 may be performed, but the present disclosure is not limited thereto. Specifically, the step of implanting the light source 100 in vivo and the step of implanting at least one photoelectric generator 200 may be performed through surgery. For example, holes are formed in the skull by using a drill, etc., to implant the light source 100 and the photoelectric generator 200 or cut and insert the muscle.

According to an implementation example of the present disclosure, the step of implanting the light source 100 includes a step of inserting the light source 100 into a gap of the nerve or the tissue. For example, the light source 100 may be implanted into the gap between a left hemisphere and a right hemisphere of the cerebrum, and the light source 100 may be implanted into a portion where the damage to the nerve or tissue is minimized other than the gap.

According to an implementation example of the present disclosure, the step of implanting the photoelectric generator 200 may be performed by the syringe, but is not limited thereto. For example, when the light source 100 may be implanted into the gap between the left hemisphere and the right hemisphere of the cerebrum, the photoelectric generator 200 may be disposed at a portion which the light 300 emitted from the light source 100 may reach, such as the cerebral cortex.

When the contents are summarized, the nerve stimulation method according to the present disclosure includes a step of first implanting the light source 100 and the photoelectric generator 200 in vivo, generating the control signal from the control unit 400 outside the living body and transmitting the generated control signal to the light source 100, and generating light 300 having a predetermined intensity and a predetermined wavelength band from the light source 100, and then irradiating the light 300 emitted from the light source 100 to the photoelectric generator 200 to generate the electricity. In this case, the electricity stimulates the nerve or tissue around the photoelectric generator 200 to treat a specific disease, etc.

Hereinafter, the present disclosure will be described in more detail through examples, but the following examples are just used for the purpose of the description, and do not intend to limit the scope of the present disclosure.

EXAMPLES

In order to form an electrode pad including a conductive composite, first, IPA (isopropyl alcohol), thinner, an anti-sticky agent, and multi-walled carbon nanotube (NWCNT) were mixed with Dragon skin polymer main chain (part A), and dispersed by using a tip sonicator to form a solution. Subsequently, a curing agent (part B) of the Dragon skin was added to the solution, and mixed through a revolution and rotation mixer, and degassed to remove internal air bubbles, thereby forming a conductive composite solution. Subsequently, an electric wire was disposed in a mold and the mold is screen-printed with the conductive composite solution to insert the electric wire into a Dragon skin-MWCNT electrode. Subsequently, when the Dragon skin was completely cured, the mold was removed and an upper portion of the electrode was coated with a polymer to form an upper electrode pad and a lower electrode pad.

A sponge layer was formed before or after forming the electrode pad, or in parallel to a process of forming the electrode pad. First, a polymer matrix was dissolved in a tetrahydrofuran (THF) solvent, and Ag micro particles was put into the polymer solution, and mixed by using the revolution and rotation mixer. Subsequently, a sponge was immersed and soaked in the solution and heated at 70° C. to evaporate the solvent. In this case, the sponge was over-turned in the process of evaporating the solvent to prevent the solution from leaning to one surface of the sponge.

Subsequently, the sponge layer was disposed on the lower electrode pad, and then the upper electrode pad was formed on the sponge layer to cross the lower electrode pad.

Figure 7:
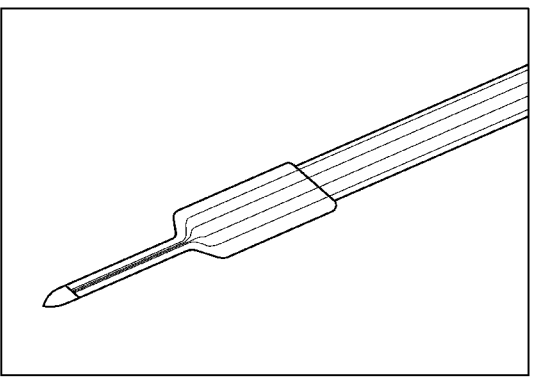
FIG. 7 is a photo of a light source according to an example of the present disclosure.

FIG. 7 is a photo of a light source according to an example of the present disclosure.

First, a multicolored micro LED having a size of 100 μm×200 μm, which is capable of emitting wavelengths of 464 nm, 530 nm, and 630 nm was formed at one end of a circuit unit capable of receiving an electric signal from the outside. Subsequently, an SU-8 resin protection layer which is a RIGIFLEX photocurable material suitable for the living body was formed on the circuit unit, and a heat dissipation layer including BN was formed at a lower end of the circuit unit to manufacture a light source.

Subsequently, an injection guide was injected into the gap between the left hemisphere and the right hemisphere of the cerebrum, and the light source was inserted into the gap through the injection guide.

Subsequently, a solar cell type photoelectric generator having a GaAs/InGaP tandem structure having a size of 3 mm×3 mm was manufactured, and at least one photoelectric generator was disposed in the cerebral cortex by using the syringe.

Subsequently, light having any one wavelength band of 464 nm, 530 nm, and 630 nm was generated in the light source through an external signal generator.

Figure 8A:
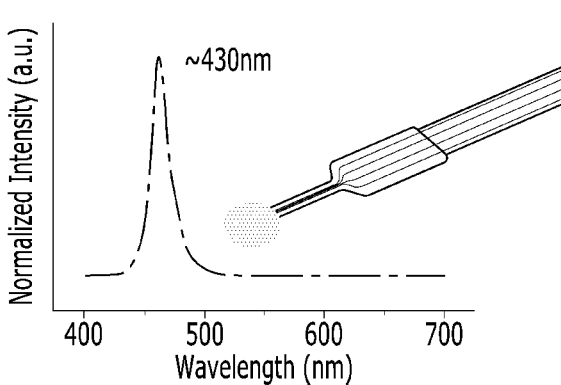
FIG. 8A to FIG. 8C are graphs related to a wavelength and an intensity of light emitted from the light source according to an example of the present disclosure.
Figure 8B:
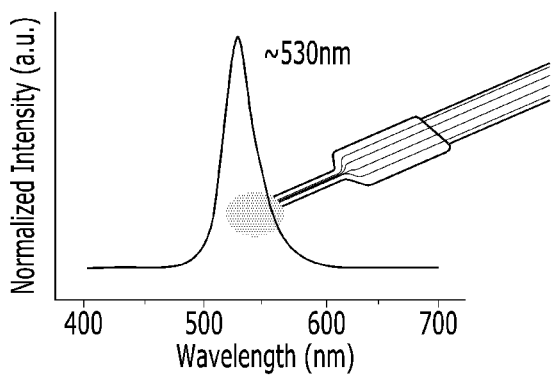
Figure 8C:
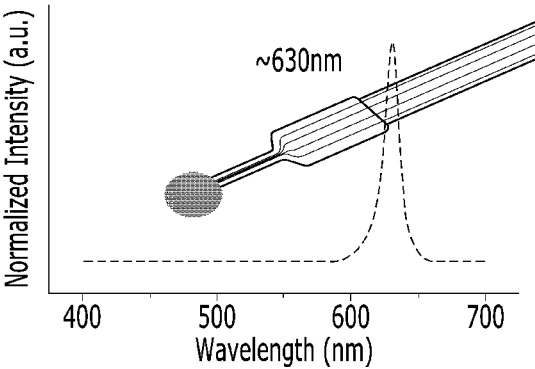

FIG. 7 is a photo of a light source according to an example of the present disclosure and FIG. 8A to FIG. 8C are graphs related to a wavelength and an intensity of light emitted from the light source according to an example of the present disclosure. Specifically, FIG. 8A is a graph related to a wavelength and an intensity of light emitted from a blue LED, FIG. 8B is a graph related to the wavelength and the intensity of the light emitted from a green LED, and FIG. 8C is a graph related to the wavelength and the intensity of the light emitted from a red LED.

Referring to FIGS. 7 and 8, it may be seen that the micro LED of the light source may selectively emit only light having a specific wavelength band.

Experimental Example 1

Optical energy of a standard condition (1,000 W/m$^2$) of AM 1.5 was irradiated to the photoelectric generator by using a solar simulator.

Figure 9:
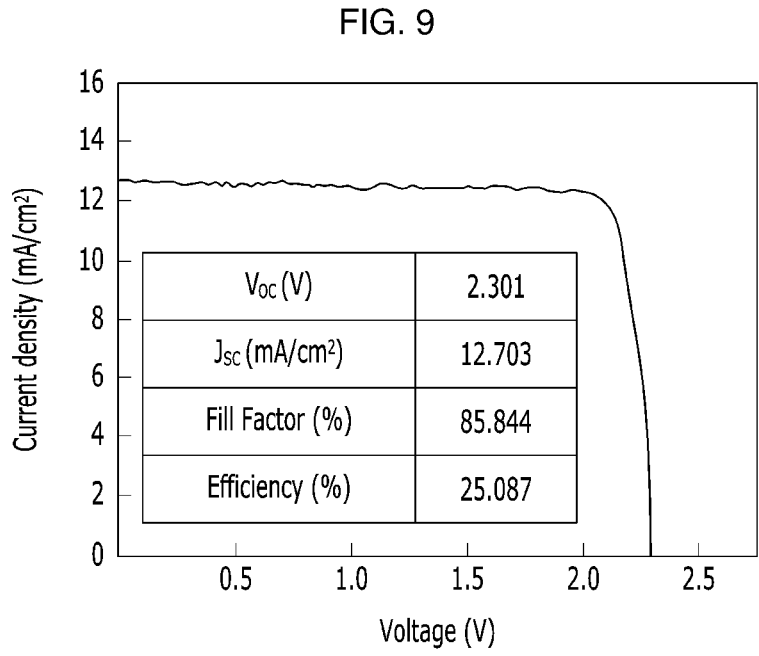
FIG. 9 is an I-V graph of the photoelectric generator according to an example of the present disclosure.

FIG. 9 is an I-V graph of the photoelectric generator according to an example of the present disclosure. Specifically, in FIG. 9, when the optical energy of AM 1.5 is irradiated to the photoelectric generator, a forward I-V graph is swept from 0 V to 2.5 V.

Referring to FIG. 9, it may be seen that Voc (open circuit voltage) of the photoelectric generator is approximately 2.3 V, J$_{SC}$ (current density) is approximately 12.7 mA/cm$^2$, a fill factor is approximately 85.8%, and transition efficiency is approximately 25%.

Experimental Example 2

Figure 10A:
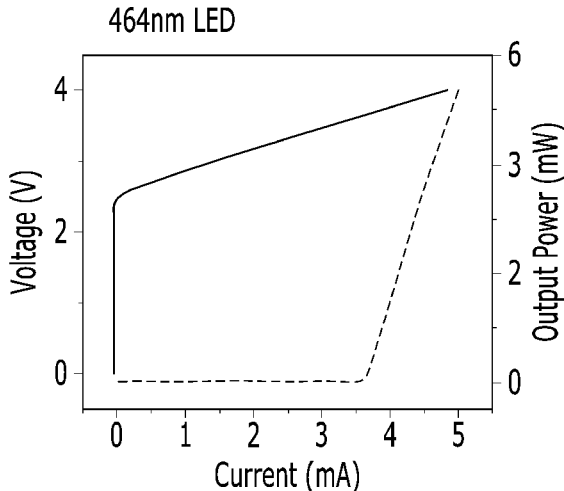
Figure 10B:
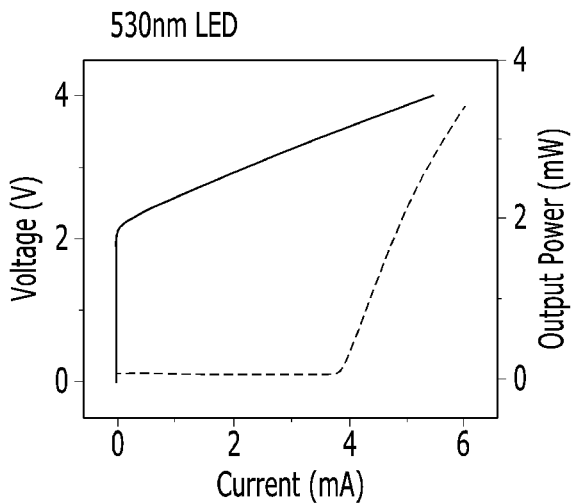
Figure 10C:
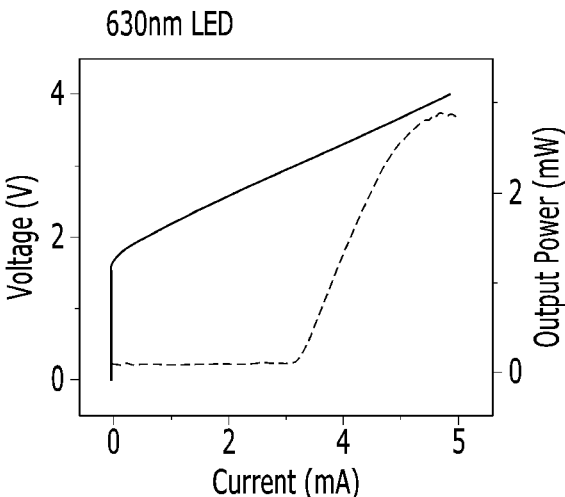

FIG. 10A to FIG. 100 are light-current-voltage (L-I-V) graphs of the light source according to an example of the present disclosure. Specifically, FIG. 10A is an L-I-V graph of the blue LED (464 nm), FIG. 10B is an L-I-V graph of the green LED (530 nm), and FIG. 10C is an L-I-V graph of the red LED (630 nm). In FIG. 10Ato FIG. 10C, a dotted line means output power, and a solid line means voltage.

Referring to FIG. 10, it may be seen that turn on voltages of the blue LED, the green LED, and the red LED are 2.2 V, 2.0 V, and 1.5 V, respectively, and as the wavelength becomes longer, the turn on voltages become smaller, and I$_{th}$(threshold current) are 3.6 mA, 3.9 mA, and 3.2 mA, respectively. It may be seen that an output power of each LED at a maximum voltage and a maximum current is lowered as the wavelength becomes longer as 5.3 mW, 3.5 mW, and 2.8 mW.

The GaAs/InGaP photoelectric generator as in the example may generate more electricity for red light, and the red light is higher in penetration for the tissue than the blue light.

Experimental Example 3

An I-V relationship of the photoelectric generator when the light is irradiated to the photoelectric generator by using the light source according to the example is examined. Specifically, the LED and the photoelectric generator were in direct contact with each other, and power of 3.5 V was applied to the micro LED.

Figure 11:
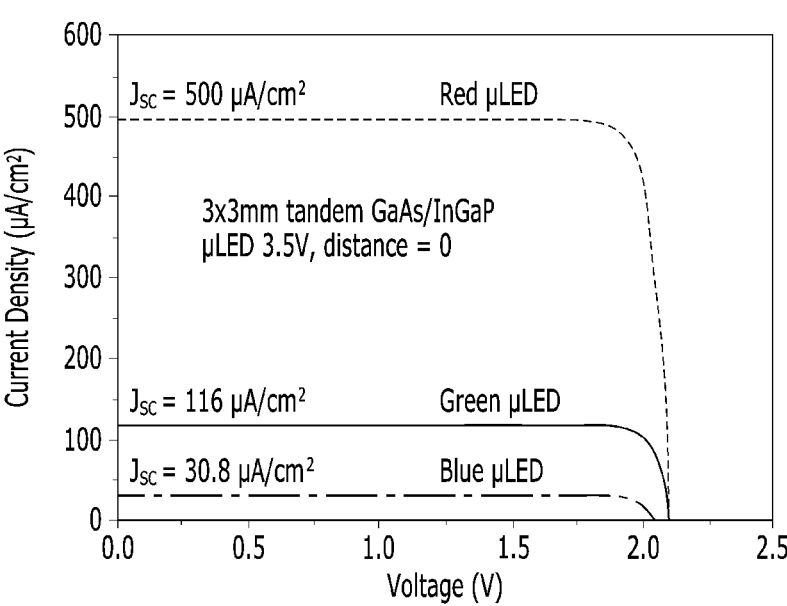
FIG. 11 is an I-V graph of the in vivo implantable nerve stimulation platform according to an example of the present disclosure.

FIG. 11 is an I-V graph of the in vivo implantable nerve stimulation platform according to an example of the present disclosure.

Referring to FIG. 11, it may be seen that the wavelength becomes longer (i.e., closer to a red color), the current density becomes higher.

The aforementioned description of the present disclosure is used for exemplification, and it may be understood by those skilled in the art that the present disclosure may be easily modified in other detailed forms without changing the technical spirit or requisite features of the present disclosure. Therefore, it should be appreciated that the aforementioned examples are illustrative in all aspects and are not restricted. For example, respective constituent elements described as single types may be distributed and implemented, and similarly, constituent elements described to be distributed may also be implemented in a coupled form.

The scope of the present disclosure is represented by claims to be described below rather than the detailed description, and it is to be interpreted that the meaning and scope of the claims and all the changes or modified forms derived from the equivalents thereof come within the scope of the present disclosure.

What is claimed is:

1. An in vivo implantable nerve stimulation platform comprising:

a light source emitting light having a plurality of wavelength bands; and a plurality of photoelectric generators, each of which generates electricity for stimulating a nerve or a tissue by the light emitted from the light source, wherein the light source and the plurality of photoelectric generators are implanted in vivo, wherein the plurality of photoelectric generators are disposed spaced apart from each other, wherein each of the plurality of photoelectric generators generates electricity according to a wavelength or an intensity of the light emitted from the light source, or a a distance between the photoelectric generator and the light source, wherein a first photoelectric generator generates the electricity according to light having a first wavelength band or light having a first intensity, and a second photoelectric generator generates the electricity according to light having a second wavelength band or light having a second intensity.

2. The in vivo implantable nerve stimulation platform of claim 1, wherein a size of the first wavelength band is larger than that of the second wavelength band, and the first intensity is smaller than the second intensity.

3. The in vivo implantable nerve stimulation platform of claim 1, wherein the first photoelectric generator is spaced apart from the light source by a first distance and the second photoelectric generator is spaced apart from the light source by a second distance.

4. The in vivo implantable nerve stimulation platform of claim 1, wherein a current density of the electricity generated by the photoelectric generator is 10 $\mu A/cm^2$ to 1,000 $\mu A/cm^2$.

5. The in vivo implantable nerve stimulation platform of claim 1, wherein each of the plurality of photoelectric generators includes InGaP and GaAs.

6. The in vivo implantable nerve stimulation platform of claim 1, wherein the light source includes an LED, a circuit unit driving the LED, an antenna supplying an operation signal to the circuit unit, a heat dissipation layer dissipating heat generated from the LED, and a protection layer protecting the LED.

7. The in vivo implantable nerve stimulation platform of claim 1, wherein the wavelength of the light emitted from the light source is 400 nm to 700 nm.

8. The in vivo implantable nerve stimulation platform of claim 1, further comprising:

a control unit controlling an operation of the implantable light source from the outside of the living body.

9. A nerve stimulation method using the in vivo implantable nerve stimulation platform of claim 1, comprising:

generating, by a control unit, a control signal for driving a light source and transmitting the generated control signal to the light source;

generating, by the light source, light having a predetermined wavelength or intensity based on the control signal; and generating, by a plurality of photoelectric generators, electricity according to a wavelength or an intensity of the generated light, wherein the plurality of photoelectric generators are disposed spaced apart from each other.

10. The nerve stimulation method of claim 9, wherein the transmitting of the control signal to the light source by the control unit is performed by wireless communication.

* * * * *